United States Patent [19]
Heller et al.

[11] Patent Number: 5,968,543
[45] Date of Patent: Oct. 19, 1999

[54] POLYMERS WITH CONTROLLED PHYSICAL STATE AND BIOERODIBILITY

[75] Inventors: Jorge Heller, Woodside; Steven Y. Ng, San Francisco, both of Calif.

[73] Assignee: Advanced Polymer Systems, Inc., Redwood City, Calif.

[21] Appl. No.: 08/986,035

[22] Filed: Dec. 5, 1997

Related U.S. Application Data

[63] Continuation-in-part of application No. 08/775,996, Jan. 3, 1997, abandoned, which is a continuation-in-part of application No. 08/583,585, Jan. 5, 1996, abandoned, and a continuation-in-part of application No. 08/583,649, Jan. 5, 1996, abandoned.

[51] Int. Cl.$^6$ .................... A61F 2/00; C08G 2/00
[52] U.S. Cl. .................... 424/425; 528/220; 528/271; 528/354; 528/392; 528/403; 528/406; 528/425; 424/422; 424/426; 424/486
[58] Field of Search .................... 528/220, 271, 528/354, 392, 403, 406, 425; 424/422, 425, 426, 486

[56] References Cited

U.S. PATENT DOCUMENTS

| | | | |
|---|---|---|---|
| 3,773,919 | 11/1973 | Boswell et al. | 424/19 |
| 4,079,038 | 3/1978 | Choi et al. | 260/47 XA |
| 4,093,709 | 6/1978 | Choi et al. | 424/19 |
| 4,131,648 | 12/1978 | Choi et al. | 424/22 |
| 4,131,662 | 12/1978 | Cekoric et al. | 264/51 |
| 4,138,344 | 2/1979 | Choi et al. | 252/1 |
| 4,180,646 | 12/1979 | Choi et al. | 528/153 |
| 4,304,767 | 12/1981 | Heller et al. | 424/78 |
| 4,532,335 | 7/1985 | Helwing | 549/335 |
| 4,757,128 | 7/1988 | Domb et al. | 528/271 |
| 4,789,724 | 12/1988 | Domb et al. | 528/176 |
| 4,857,311 | 8/1989 | Domb et al. | 424/78 |
| 4,888,176 | 12/1989 | Langer et al. | 424/426 |
| 4,946,931 | 8/1990 | Heller et al. | 528/230 |
| 4,957,998 | 9/1990 | Heller et al. | 528/220 |
| 5,145,684 | 9/1992 | Liversidge et al. | 424/489 |
| 5,518,730 | 5/1996 | Fuisz | 424/426 |
| 5,620,697 | 4/1997 | Törmälä et al. | 424/426 |
| 5,626,862 | 5/1997 | Brem et al. | 424/426 |
| 5,651,986 | 7/1997 | Brem et al. | 424/484 |

FOREIGN PATENT DOCUMENTS

| | | |
|---|---|---|
| 0419156 | 3/1991 | European Pat. Off. . |
| 91/03510 | 3/1991 | WIPO . |
| 96/03984 | 2/1996 | WIPO . |

OTHER PUBLICATIONS

K. Athanasiou et al., "Sterilization, toxicity, biocompatibility and clinical applications of polylactic acid/polyglycolic acid copolymers", *Biomaterials*, 17, 93–102 (1996).

R. Auerbach et al., "Site–specific drug delivery to the lung", *Polymers for Advanced Technologies*, 3, 323–329 (1992).

H. Brem et al., "Intraoperative chemotherapy using biodegradable polymers: safety and effectiveness . . . ", Proc. of the Amer. Society of Clinical Onc., Dallas, TX, May 17, 1994.

H. Brem et al., "Polymers as controlled drug delivery devices for the treatment of malignant brain tumors", *Eur. J. Pharm. Biopharm.*, 39, 2–7 (1993).

H. Brem et al., "Interstitial chemotherapy with drug polymer implants for the treatment of recurrent gliomas", *J. Neurosurg.* 74, 441–446 (1991).

(List continued on next page.)

Primary Examiner—Samuel A. Acquah
Attorney, Agent, or Firm—Heller Ehrman White & McAuliffe

[57] ABSTRACT

Polymers useful as orthopedic implants or vehicles for the sustained delivery of pharmaceutical, cosmetic and agricultural agents are prepared in such a manner that the rate and degree to which they are hydrolyzed can be controlled without addition of exogenous acid. This control results from the incorporation of esters of short-chain α-hydroxy acids such as esters of glycolic acid, lactic acid or glycolic-co-lactic acid copolymer into the polymer chain and variation of the amount of these esters relative to the polymer as a whole.

30 Claims, 2 Drawing Sheets

OTHER PUBLICATIONS

A. Domb et al., "Controlled delivery of water soluble and hydrolytically . . . ", *Polymer Preprints* 32, 219–220 (1991).

A. Domb et al., "Polyanhydrides. I. Preparation of high molecular weight polyanhydrides", *J. of Polymer Science: Part A, Polymer Chemistry,* 25, 3373–3386 (1987).

S. Grossman et al., "The intracerebral distribution of BCNU delivered . . . ", *J. Neurosurg.,* 76, 640–647 (1992).

J. Heller, "Poly(ortho esters)", *Adv. in Polymer Sci.,* 107, 41–92 (1993).

J. Heller et al., "Preparation of polyacetals by the reaction of divinyl ethers and polyols", *J. Polymer Sci., Polymer Letters Ed.,* 18, 293–297 (1980).

H. Jampel et al., "In vitro release of hydrophobic drugs . . . ", *Opthalmic Surgery,* 22, 676–680 (1991).

I. Kaetsu et al., "Biodegradable implant composites for local therapy", *J. of Controlled Release,* 6, 249–263 (1987).

R. Langer, "1994 Whitaker Lecture: Polymers for drug delivery and tissue engineering", *Ann. Biomed. Eng.,* 23, 101–111 (1995).

R. Langer et al., "Biocompatibility of polymeric delivery systems for macromolecules", *J. of Biomedical Materials Research*, 15, 267–277 (1981).

R. Langer et al., "Polymers for the sustained release of proteins and other macromolecules", *Nature,* 263, 797–800 (1976).

K. Leong et al., "Bioerodible polyanhydrides as drug-carrier matrices. II. Biocompatibility . . . ", *J. of Biomedical Materials Research,* 20, 51–64 (1986).

K. Leong et al., "Bioerodible polyanhydrides as drug-carrier matrices. I: Characterization . . . ", *J. of Biomedical Materials Research,* 19, 941–955 (1985).

W. Rhine et al., "Polymers for sustained macromolecule release: procedures to fabricate . . . ", *J. of Pharmaceutical Science,* 69, 265–270 (1980).

H. Rosen et al., "Bioerodible polyanhydrides for controlled drug delivery", *Biomaterials,* 4, 131–133 (1983).

L. Seymour et al., "Poly(ortho ester) matrices for controlled release of the antitumor agent 5-fluorouracil", *J. Controlled Release,* 31, 201–206 (1994).

R. Straw et al., "Local slow-release cisplatin therapy after marginal local tumor resection", *Front. Osteosarcoma Res.,* 121–123 (1993).

R. Tamargo et al., "Interstitial chemotherapy of the 9L gliosarcoma: Controlled release polymers for drug delivery in the brain", *Cancer Research,* 53, 329–333 (1993).

T. Tomita, "Interstitial chemotherapy for brain tumors: review", *J. of Neuro–Oncology,* 10, 57–74 (1991).

K. Walter et al., "Interstitial taxol delivered from a biodegradable polymer implant against experimental malignant glioma", *Cancer Research,* 54, 2207–2212 (1994).

S. Yolles et al., "Sustained delivery of drugs from polymer/drug mixtures", *Polymer News,* 1, 9–15 (1970).

POLYMERS WITH CONTROLLED PHYSICAL STATE AND BIOERODIBILITY

CROSS REFERENCE TO RELATED APPLICATIONS

This application is a continuation-in-part of our Application Ser. No. 08/775,996, filed Jan. 3, 1997, abandoned which is in turn a continuation-in-part of our then Applications Ser. Nos. 08/583,585 and 08/583,649, both filed Jan. 5, 1996, and now abandoned. Each of these applications is incorporated herein by reference.

BACKGROUND OF THE INVENTION

A. Field of the Invention

The present invention relates to polymers which have pharmaceutical, cosmetic and clinical applications. In particular, this invention relates to polymers whose mechano-physical state and the rate at which they erode in a biological environment are controllable in degrees by their molecular structures, and their use as vehicles for sustained-release delivery of active agents or as implants.

B. Description of the Prior Art

Interest in synthetic biodegradable polymers for the systemic delivery of therapeutic agents began in the early 1970's with the work of Yolles et al., *Polymer News* 1:9–15 (1970) using poly(lactic acid). Since that time, numerous other polymers have been prepared and investigated as bioerodible matrices for the controlled release of therapeutic agents.

U.S. Pat. Nos. 4,079,038, 4,093,709, 4,131,648, 4,138,344 and 4,180,646 disclose biodegradable or bioerodible poly(ortho ester)s. These polymers are formed by a reaction between an ortho ester (or orthocarbonate) such as 2,2-diethoxytetrahydrofuran and a diol such as 1,4-cyclohexanedimethanol. The reaction requires elevated temperature and reduced pressure and a relatively long reaction time. Drugs or other active agents are retained in the polymer matrix to be released as the polymer biodegrades due to hydrolysis of the labile linkages.

U.S. Pat. No. 4,304,767 discloses polymers prepared by reacting a polyol with a polyfunctional ketene acetal. These polymers represent a significant improvement over those of U.S. Pat. Nos. 4,079,038, 4,093,709, 4,131,648, 4,138,344 and 4,180,646, since synthesis proceeds readily at room temperature and atmospheric pressure, and the resulting polymers have superior properties.

Further polymers are disclosed in U.S. Pat. No. 4,957,998. These polymers contain acetal, carboxy-acetal and carboxy-ortho ester linkages, and are prepared by a two-step process beginning with the reaction between a polyfunctional ketene acetal and a compound containing a vinyl ether, followed by reaction with a polyol or polyacid.

Still further polymers of a similar type are disclosed in U.S. Pat. No. 4,946,931. The polymers are formed by a reaction between a compound containing a multiplicity of carboxylate functions and a polyfunctional ketene acetal. The resulting polymers have very rapid erosion times.

Despite the ease with which the ortho ester linkage hydrolyses, poly(ortho ester)s known in the prior art are extremely stable materials when placed in an aqueous buffer, or when residing in the body. This stability is attributable to the extreme hydrophobicity of the poly(ortho ester)s which severely limits the amount of water that can penetrate the polymer. To achieve useful erosion rates, therefore, acidic excipients must be physically incorporated into the polymer. While this allows control over erosion rates, the physically incorporated acidic excipient can diffuse from the polymer matrix at varying rates, leaving a matrix that is completely depleted of excipient while the polymer still has a very long lifetime remaining.

The disclosures of the documents listed in this section and elsewhere throughout this application are incorporated herein by reference.

SUMMARY OF THE INVENTION

It has now been discovered that polymers useful as orthopedic implants or vehicles for the sequestration and sustained delivery of drugs, cosmetic agents and other beneficial agents can be prepared in such a manner that the rate and degree to which they are hydrolyzed by contact with bodily fluids at normal body temperature and pH can be controlled without addition of exogenous acid. This discovery resides in the incorporation of esters of short-chain α-hydroxy acids such as esters of glycolic acid, lactic acid or glycolic-co-lactic acid copolymer into the polymer chain and variation of the amount of these esters relative to the polymer as a whole.

In the presence of water, these esters, when incorporated into the polymer chain, are readily hydrolyzed at a body temperature of 37° C. and a physiological pH, in particular at a pH of 7.4, to produce the corresponding α-hydroxy acids. The α-hydroxy acids then act as an acidic excipient to control the hydrolysis rate of the polymer. When the polymer is used as a vehicle or matrix entrapping an active agent, the hydrolysis of the polymer causes release of the active agent.

In addition, the mechano-physical state of the polymer may also be controlled. This is achieved by the inclusion of the residues of certain diols in selected proportions relative to the polymer as a whole. For example, a high content of the residue of trans-cyclohexanedimethanol relative to a "soft" diol (definition of which is given below) produces a relatively rigid polymer chain and a more solid substance, and by decreasing the trans-cyclohexanedimethanol content relative to the "soft" diol, the polymer will change progressively through the stages of a rigid thermoplastic, a soft thermoplastic, a low melting solid to an ointment-like (viscous liquid) material, and any stage in between.

The polymers of the present invention are prepared by condensation reactions between diketene acetals and polyols, preferably diols, and the variation in mechano-physical state and rate of hydrolysis (bioerodibility) is achieved by the selection and use of combinations of different types of diols.

DETAILED DESCRIPTION OF THE INVENTION

I. Definitions

Figure 1:
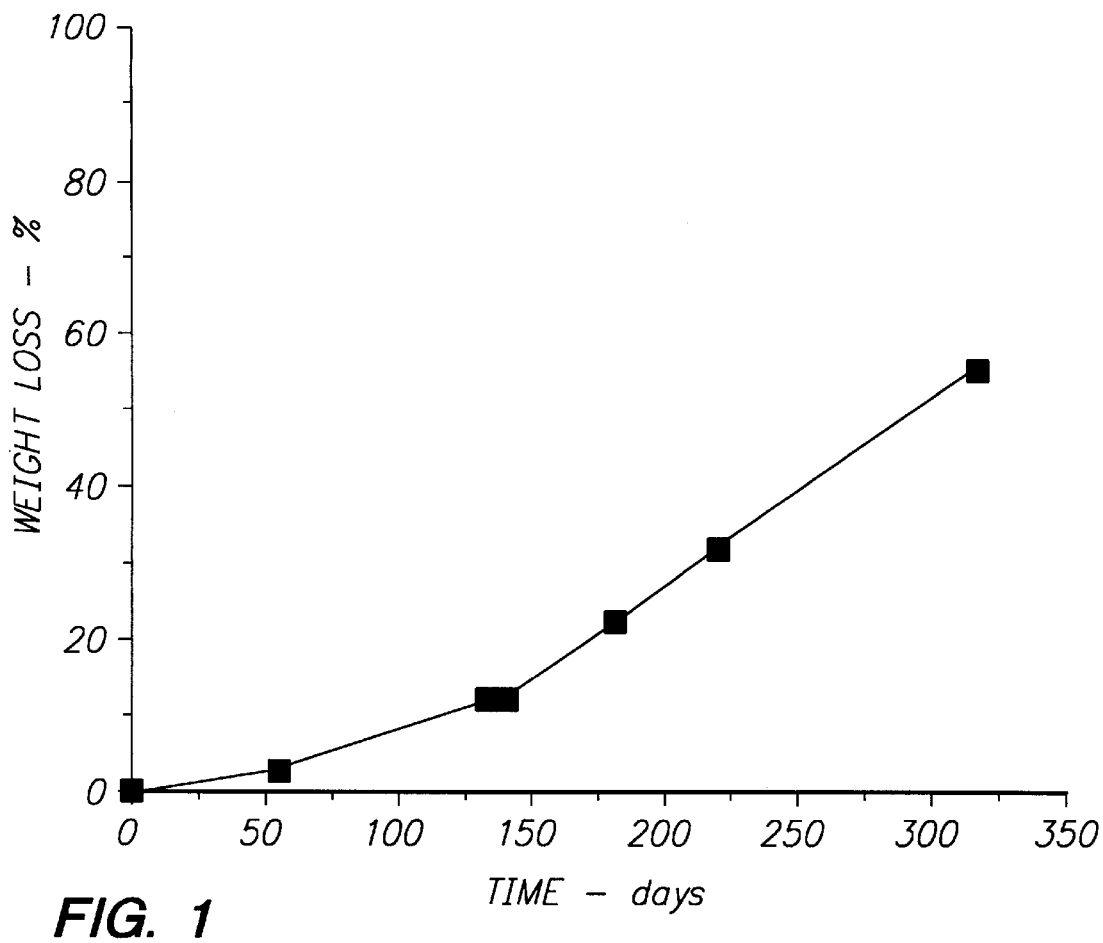
FIG. 1 shows the rate of weight loss of a polymer not of this invention containing no α-hydroxy acid containing units (a comparative example).

Unless defined otherwise in this specification, all technical and scientific terms are used herein according to their conventional definitions as they are commonly used and understood by those of ordinary skill in the art of synthetic chemistry, pharmacology and cosmetology.

The term "matrix" denotes the physical structure of the polymer. Solid matrices essentially retain the active agent in a manner preventing release of the agent until the polymer erodes or decomposes.

The terms "vehicle" and "carrier" denote an ingredient that is included in a composition such as a pharmaceutical or cosmetic preparation for reasons other than a therapeutic or other biological effect. Functions served by vehicles and carriers include transporting an active agent to a site of interest, controlling the rate of access to, or release of, the active agent by sequestration or other means, and facilitating the application of the agent to the region where its activity is needed.

The terms "controlled release", "sustained release" and similar terms are used to denote a mode of active agent delivery that occurs when the active agent is released from the vehicle or carrier at an ascertainable and manipulatable rate over a period of time, rather than dispersed immediately upon ingestion or application. Controlled or sustained release may extend for hours, days or months, and may vary as a function of numerous factors. In the present invention, an important determinant of the rate of delivery is the rate of hydrolysis of the linkages between and within the units of the polymer. The rate of hydrolysis in turn may be controlled by the composition of the polymer and the number of hydrolyzable bonds in the polymer. Other factors include particle size, particle composition, particle hydration, acidity of the medium (either internal or external to the matrix), solubility of the active agent in the matrix and molecular weight and charge density of the active agent.

The term "active agent" is intended to include any compound or mixture of compounds which produces a beneficial or useful result. Active agents are distinguishable from such components as vehicles, carriers, diluents, lubricants, binders and other formulating aids, and encapsulating or otherwise protective components. Examples of active agents are pharmaceutical, agricultural or cosmetic agents. Suitable pharmaceutical agents include antigens, antibodies, vaccines, hormones (for example, estrogens, progestins, androgens, adrenocortical steroids, insulin, erythropoietin and the like), vitamins, enzymes, proteins, naturally occurring or bioengineered substances, anti-infectives (including antibiotics, antivirals, fungicides, scabicides or pediculicides), antipsychotic agents (for example, phenothiazines including chlorpromazine, triflupromazine, mesoridazine, piperacetazine and thioridazine; thioxanthenes including chlorprothixene; and the like), anti-anxiety agents (for example, benzodiazepines including diazepam, alprazolam, clonazepam, oxazepam; and barbiturates), antidepressants (including tricyclic antidepressants and monoamine oxidase inhibitors including imipramine, amitriptyline, doxepin, nortriptyline, amoxapine, tranylcypromine, phenelzine and the like), stimulants (for example, methylphenidate, doxapram, nikethamide and the like), narcotics (for example, morphine, meperidine, codeine and the like), analgesic-antipyretics and anti-inflammatory agents (for example, aspirin, ibuprofen, naproxen and the like), local anesthetics (for example, procaine, lidocaine, tetracaine and the like), fertility control agents, chemotherapeutic and anti-neoplastic agents (for example, mechlorethamine, cyclophosphamide, 5-fluorouracil, thioguanine, carmustine, lomustine, melphalan, chlorambucil, streptozocin, methotrexate, vincristine, bleomycin, vinblastine, vindesine, dactinomycin, daunorubicin, doxorubicin, tamoxifen and the like), cardiovascular and anti-hypertensive agents (for example, procainamide, amyl nitrite, nitroglycerin, propranolol, metoprolol, prazosin, phentolamine, trimethaphan, captopril, enalapril and the like), drugs for the therapy of pulmonary disorders, anti-epilepsy agents (for example, phenytoin, ethotoin and the like), antipruritics, astringents, anti-hidrotics, keratolytic agents, keratoplastic agents, rubefacients, sunscreens, pigmentation agents or emollients. The term "active agents" further includes biocides such as fungicides, pesticides, and herbicides, plant growth promoters or inhibitors, preservatives, disinfectants, air purifiers and nutrients.

"Sequestration" is the confinement or retention of an active agent within the internal spaces of a polymer matrix. Sequestration of an active agent within the matrix may limit the toxic effect of the agent, prolong the time of action of the agent in a controlled manner, permit the release of the agent in a precisely defined location in an organism, or protect unstable agents against the action of the environment.

The term "unit" denotes an individual segment of a polymer chain, which, for the purpose of this invention, consists of the residue of a diketene acetal molecule and the residue of a polyol. The specific structure of a "unit" formed from a diketene acetal molecule with a diol is represented by Formula I(unit) in the following sections.

An "$\alpha$-hydroxy acid containing" unit denotes an individual unit, the amount of which relative to the polymer as a whole determines the rate of hydrolysis (or bioerodibility) of the polymer, and in turn, the release rate of the active agent. The specific structure of an "$\alpha$-hydroxy acid containing" unit is represented by Formula I(a) in the following sections.

The terms "hard" and "soft" units denote individual units of polymer, the contents of which relative to the polymer as a whole determine the mechano-physical state of the polymer. The specific structures of "hard" and "soft" units are represented by Formulas I(b) and I(c) respectively in the following sections.

The term "polyol" refers to a chemical compound having more than one hydroxy (—OH) functional group.

The term "diol" refers to a chemical compound having two hydroxy (—OH) groups. For the purpose of this invention, the diols are classified into three groups: "$\alpha$-hydroxy acid containing" diols, "hard" diols, and "soft" diols. The specific structures of these three types of diols are represented by Formulas III(a), III(b), and III(c) respectively in the following sections.

The term "alkyl" denotes a branched or unbranched saturated hydrocarbon radical having from one to the number of carbon atoms designated (e.g., $C_1$–$C_{12}$ alkyl). Examples of alkyl include methyl, ethyl, n-propyl, isopropyl, n-butyl, t-butyl, n-hexyl, n-octyl and the like.

The term "alkylene" denotes a branched or unbranched saturated divalent radical having from one to the number of carbon atoms designated (e.g., $C_1$–$C_{12}$ alkylene). Examples of alkylene include methylene (—$CH_2$—), ethylene (—$CH_2CH_2$—), isopentylene (—$CH_2$—$CH(CH_3)$—$CH_2$—$CH_2$—), n-octylene (—$(CH_2)_8$—) and the like.

The terms "bioerodible" and "bioerodibility" refer to the degradation, disassembly or digestion of the polymer by action of a biological environment, including the action of living organisms and most notably at physiological pH and temperature. A principal mechanism for bioerosion of the polymers of the present invention is hydrolysis of linkages between and within the units of the polymer. In the present invention, the rate of hydrolysis of the linkages may be determined by the content of the "α-hydroxy acid containing" units relative to the polymer as a whole.

The terms "flexible" and "rigid" refer to the mechanophysical state of the polymer. A "flexible" chain generally contains a relative high amount of "soft" units and may impart a liquid or ointment-like quality, while a "rigid" chain generally contains a relative high amount of "hard" units and tends to impart a solid, plastic-like consistency.

The term "polymer hydrolysis", for the purpose of this invention, refers to the hydrolysis of the linkages between and within the units of the polymer.

The term "mole percent", for the purpose of this invention, refers to the number of a particular type of unit (e.g., the "α-hydroxy acid containing" unit, "hard" unit or "soft" unit) in 100 individual units of the polymer chain.

The term "molecular weight" refers to the sum of the weights of all atoms in the polymer chain.

II. Structure of the Polymer

The polymer of the present invention is represented by the following general formula

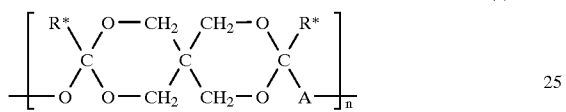

(1)

where A is —O—$R^1$—, —O—$R^2$— or (—O—$R^3$)$_q$—; the definitions of $R^1$, $R^2$, $R^3$ and q are specifically given below; $R^*$ is a $C_1$–$C_4$ alkyl; and n is at least 5; provided that the polymer contains at least 0.1 mole percent of "α-hydroxy acid containing" units.

Each individual "unit" of the polymer represented by the following formula

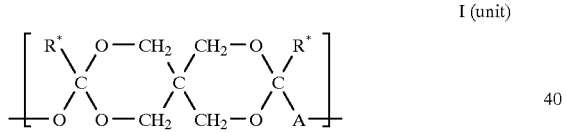

I (unit)

may be an "α-hydroxy acid containing" unit (where A is —O—$R^1$—), a "hard" unit (where A is —O—$R^2$—) or a "soft" unit (where A is —(O—$R^3$)$_q$—) provided that the polymer contains at least 0.1 mole percent of "α-hydroxy acid containing" units.

An "α-hydroxy acid containing" unit is represented by the following formula

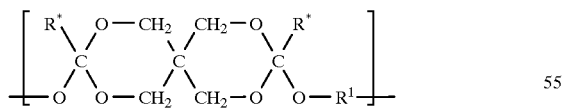

I (a)

where $R^*$ is a $C_1$–$C_4$ alkyl and $R^1$ is

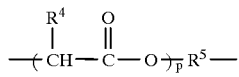

in which:
p is 1–10;
$R^4$ is hydrogen or a $C_1$–$C_6$ alkyl; and $R^5$ is

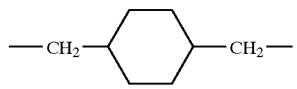

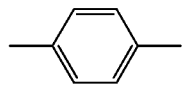

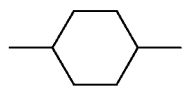

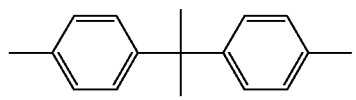

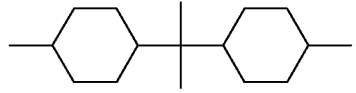

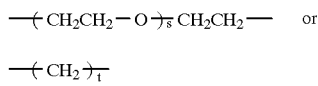   or

—(CH$_2$)$_t$— where:
s is 1 to 100; and
t is 1 to 12.

A "hard" unit is represented by the following formula

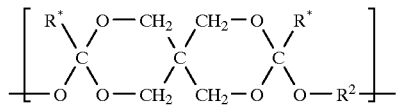

I (b)

where $R^*$ is a $C_1$–$C_4$ alkyl and $R^2$ is

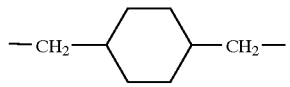

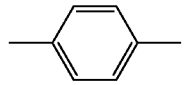

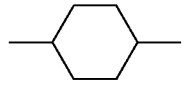

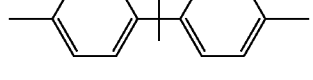

or

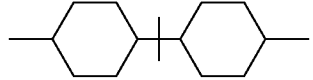

A "soft" unit is represented by the following formula

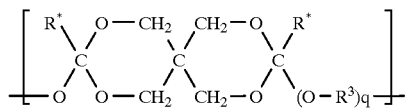

I (c)

where R* is a $C_1$–$C_4$ alkyl; q is 1 to 20; and when q is 1, $R^3$ is

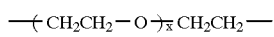

—$(CH_2)_y$—   or

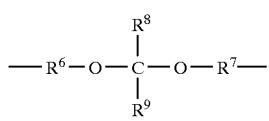

in which:
x is 1 to 100;
y is 1 to 12;
$R^6$ and $R^7$ are independently a $C_1$–$C_{12}$ alkylene;
$R^8$ is hydrogen or a $C_1$–$C_6$ alkyl; and
$R^9$ is a $C_1$–$C_6$ alkyl; or
$R^8$ and $R^9$ taken together are a $C_3$–$C_{10}$ alkylene; and when q is 2 to 20, each $R^3$ may be the same or different and is selected from the group consisting of

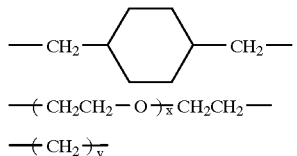

—$(CH_2CH_2—O)_{\overline{x}}CH_2CH_2$—

—$(CH_2)_{\overline{y}}$—

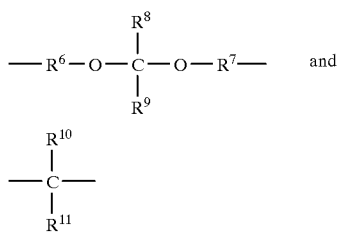

where x, y, $R^6$, $R^7$, $R^8$ and $R^9$ are as defined above, $R^{10}$ is hydrogen or a $C_1$–$C_4$ alkyl, and $R^{11}$ is a $C_1$–$C_4$ alkyl.

The structure of the polymer of this invention, as shown in general Formula I, is one of alternating residues of the diketene acetal and a diol, with each adjacent pair of diketene acetal residues being separated by the residue of one polyol, preferably a diol.

The rate of hydrolysis and mechano-physical state of the polymer are determined by the contents of the three types of units. Generally, the polymer may consist of 5 to 1000 individual units.

The composition of the polymer may also be conveniently expressed in mole percentage. The "α-hydroxy acid containing" unit constitutes about 0.1 to 100 mole percent of the polymer as a whole. Each of the "hard" and "soft" units constitutes about 0–99.9 mole percent of the polymer.

It is also understood that the present invention includes cross-linked polymers prepared from a diketene acetal and a mixture of polyols which comprises one or more polyols having more than two hydroxy functional groups.

III. Preferred Embodiments

The preferred embodiment of the present invention is the polymer of Formula (I) where n is about 5 to about 1000, more preferably about 20 to about 500, and most preferably about 30 to about 300. The molecular weight of the polymer consequently ranges from about 1,000 to about 500,000.

Expressed in terms of mole percent of the "hard" unit relative to the polymer as a whole, preferred polymers for liquid or ointment-like compositions are those in which the "hard" unit constitutes about 20 mole percent or less. Likewise, preferred polymers for more solid compositions are those in which the "hard" unit constitutes from about 60 mole percent to about 99.9 mole percent.

Polymers having a higher content of the "α-hydroxy acid containing" unit will have a higher rate of bioerodibility. Preferred polymers are those in which the "α-hydroxy acid containing" units constitute preferably from about 1 to about 50 mole percent, more preferably from about 2 to about 30 mole percent, for example from about 5 to about 30 mole percent, especially from about 10 to about 30 mole percent.

With respect to the individual "α-hydroxy acid containing" unit of Formula I(a) where $R^1$ is

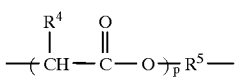

p is preferably 1 to 6, more preferably 1 to 4, most preferably 1 or 2; $R^4$ is preferably hydrogen or methyl; and in the above definitions of $R^5$, s is preferably 2 to 12, more preferably 2 to 6 and most preferably 2; and t is preferably 4 to 12, more preferably 4 to 6 and most preferably 6.

With respect to the individual "hard" unit of Formula I(b), $R^2$ is preferably

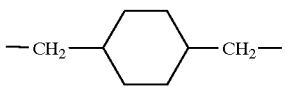

With respect to the individual "soft" unit of Formula I(c), q is preferably 1 to 6 and more preferably 1 to 3; and in the definitions of $R^3$, x is preferably 2 to 12, more preferably 2 to 6 and most preferably 2; y is preferably 4 to 12, more preferably 4 to 6 and most preferably 6; $R^6$ and $R^7$ are preferably identical, more preferably an unbranched $C_4$–$C_{12}$ alkylene and most preferably an unbranched $C_6$–$C_{12}$ alkylene; $R^8$ is preferably hydrogen; $R^9$ is preferably methyl; $R^{10}$ is preferably hydrogen and $R^{11}$ is preferably methyl.

Further preferred embodiments are those in which the diol mixture contains one of the various specific diols listed in Example 2, as well as various combinations of diols used in Examples 3 and 4.

IV. Preparation of the Polymer

The polymer of this invention is prepared by the reaction of a diketene acetal of Formula II

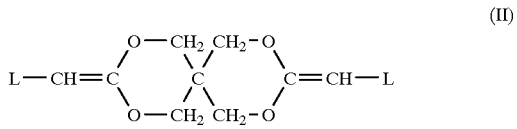

(II)

where L is hydrogen or a $C_{1-3}$ alkyl, with a diol of Formula III(a), or a mixture of two or three diols of Formulas III(a)–III(c) in selected proportions, with the proviso that at least 0.1% of the total diol mixture is the diol of Formula III(a):

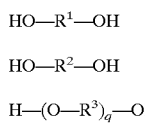

$$\text{HO—R}^1\text{—OH} \quad \text{III(a)}$$

$$\text{HO—R}^2\text{—OH} \quad \text{III(b)}$$

$$\text{H—(O—R}^3)_q\text{—OH} \quad \text{III(c)}$$

where q, $R^1$, $R^2$ and $R^3$ are as defined above.

The "α-hydroxy acid containing" unit of Formula I(a) is formed by the reaction between the diketene acetal of Formula II with a diol of Formula III(a).

Similarly, the "hard" unit of Formula I(b) is formed by the reaction between the diketene acetal of Formula II with a diol of Formula III(b), and the "soft" unit of Formula I(c) is formed by the reaction between the diketene acetal of Formula II with a diol of Formula III(c).

To form the polymer using diols of the three types, a diol mixture is formed with selected proportions based on the desired characteristics of the polymer. The diol mixture contains at least 0.1 mole percent of the diol of Formula III(a).

The invention includes polymers which are prepared from a mixture of the three types of diols as well as polymers prepared from only the diol of Formula III(a) or a mixture of two of the three types of diols, one of which is the diol of Formula III(a). It also includes polymers prepared from a mixture of diols which contains two or more diols of the same type.

The preparation of the diketene acetal of Formula II is disclosed in U.S. Pat. Nos. 4,304,767 and 4,532,335. The diols are prepared according to methods known in the art. Some of the diols suitable for the present invention are also commercially available. For example, trans-cyclohexane-dimethanol can be purchased from Cros-Organics (New Jersey). The preparation of diols, in particular the "soft" diols of Formula III(c) is generally disclosed in Heller et al., *J. Polymer Sci., Polymer Letters Ed.* 18:293–297 (1980), by reacting an appropriate divinyl ether with an appropriate diol. The "α-hydroxy acid containing" diol of Formula III(a) that comprises a polyester moiety may be prepared by reacting a selected diol (which is expressed as HO—$R^5$—OH) with between 0.5 and 5 molar equivalents of a cyclic ester of an α-hydroxy acid, and allowing the reaction to proceed at 100–200° C. for a period of time ranging from about 12 hours to about 48 hours. Although particular solvents are not required for this reaction, organic solvents such as dimethylacetamide, dimethyl sulfoxide, dimethylformamide, acetonitrile, pyrrolidone, tetrahydrofuran, and methylbutyl ether may be used.

Once made, the "α-hydroxy acid containing" diol of Formula III(a) and the diols of Formulas III(b) and/or III(c) with selected proportions are mixed with the diketene acetal of Formula II, in accordance with the 1:1 stoichiometric ratio of total number of moles of diketene acetal to total number of moles of diols, in a suitable solvent at ambient temperature. The condensation reaction between the diketene acetal and the diols is carried out under conditions which are well known to those skilled in the art and will also be readily apparent from the structures of the reactants themselves. Suitable solvents are polar aprotic solvents, such as dimethylacetamide, dimethyl sulfoxide, dimethylformamide, acetonitrile, pyrrolidone, tetrahydrofuran, and methylbutyl ether, and the like. Catalysts are not required for this reaction, but when used, suitable catalysts are iodine in pyridine, p-toluenesulfonic acid; Lewis acids (such as boron trichloride, boron trifluoride, boron trichloride etherate, boron trifluoride etherate, stannic oxychloride, phosphorous oxychloride, zinc chloride, phosphorous pentachloride, antimony pentafluoride, stannous octoate, stannic chloride, diethyl zinc, and mixtures thereof); and Bronsted catalysts (such as polyphosphoric acid, crosslinked polystyrene sulfonic acid, acidic silica gel, and mixtures thereof). A typical amount of catalyst used is about 0.2% by weight relative to the diketene acetal. Smaller or larger amounts can also be used, such as 0.005% to about 2.0% by weight relative to the diketene acetal of Formula II.

Once the reaction is complete, the reaction mixture is allowed to cool to room temperature. About ten volumes of a precipitant such as anhydrous methanol or hexane at room temperature are then added, and the precipitated polymer may be collected by filtration or decanting, and dried in a vacuum oven at 30–40° C.

The rigidity or flexibility of the polymer is determined by the proportions of the "hard" and "soft" units in the polymer structure, with greater rigidity achieved by including greater proportions of the "hard" diol of Formula III(b) in the diol mixture.

The bioerodibility of the polymer is determined by the proportion of the hydrolyzable α-hydroxy acid ester groups, with greater bioerodibility achieved by including greater proportions of the "α-hydroxy acid containing" diol of Formula III(a) in the diol mixture.

Thus, both characteristics of the resulting polymer prepared from the reaction between the diketene acetal of Formula II and a mixture of the diols, are controlled by the ratio of quantities of the three types of diols in the diol mixture.

It is also understood that the present invention encompasses cross-linked polymers which are prepared by employing one or more polyols having more than two hydroxy functional groups. Such cross-linked polymers may be prepared preferably by first reacting the diketene acetal with a mixture of diols comprising a diol of Formula III(a) and optionally a diol of Formula III(b) and/or a diol of Formula III(c) followed by addition of the polyol(s) having more than two hydroxy functional groups. Alternatively, the polyol(s) having more than two hydroxy functional groups may be added simultaneously with the diol of Formula III(a) and other diols. Polyols having more than two hydroxy functional groups suitable for the preparation of the cross-linked polymers may be the straight or branched chain type, including polyhydroxyl compounds such as 1,2,3-propanetriol, 1,2,5-pentanetriol, 1,2,6-hexanetriol, 1,3,5-pentanetriol, 1,2,4-butanetriol, 1,4,7-heptanetriol, 1,5,10-decanetriol, 1,5,12-dodecanetriol, 1,2,3,4,5,6-hexane-hexol and the like. Other representative polyols of the type are described in U.S. Pat. No. 4,304,767. The reaction conditions (e.g., suitable solvents and reaction temperatures) and procedures for the preparation of the cross-linked polymers are similar to those described above for the preparation of the polymers employing only the diols, and are also described in U.S. Pat. No. 4,304,767.

V. Use of the Polymer

The present polymers can be used for any use in which bioerodible polymers are usable, such as vehicles for the sustained release of an active agent or as orthopedic implants.

To use the polymer as a sustained-release vehicle, the active agent must be incorporated into a matrix of the polymer or encapsulated within a capsule (or a "microcapsule" or "nanocapsule", as those terms are sometimes used) of the polymer. Methods for the preparation of sustained-release dosage forms using biodegradable polymers are well known in the art, as discussed in the references cited in the "Description of the Prior Art" section of this application, and in other references familiar to those of ordinary skill in the art; so that a person of ordinary skill in the art would have no difficulty, having regard to that skill and this disclosure, in preparing sustained-release formulations using the polymer of this invention. Suitable active agents include therapeutic agents such as pharmaceutical or pharmacological active agents, e.g. drugs and medicaments, as well as prophylactic agents, diagnostic agents, and other chemicals or materials useful in preventing or treating disease. The compositions of this invention are particularly useful for the therapeutic treatment of humans and other mammals, but may also be used for other animals. In addition, the sustained-release compositions of this invention may also be used for the release of cosmetic and agricultural agents, or for the release of biocides, such as fungicides or other pesticides, into an environment where prolonged release of the active agent is desired.

In the case of matrix formulations, the polymer is first mixed with the active agent. High homogeneity may be achieved by mixing the polymer in its heat softened state with the active agent, followed by lowering the temperature to harden the composition. Alternatively, the polymer can be dissolved in an appropriate casting solvent, such as tetrahydrofuran, methylene chloride, chloroform or ethyl acetate, and the active agent can then be dispersed or dissolved in the polymer solution, followed by evaporating the solvent to achieve the finished composition. Another method is grinding a solid polymer material into powder which is then mixed with a powdered active agent. The active agent may also be incorporated into the mixture of monomers before polymerization provided that it is stable under the polymerization conditions and does not interfere with the polymerization reaction.

If the active agent is one that is unstable at elevated temperatures (e.g. above 40° C.), or in the presence of organic solvents or organic solvent/water mixtures, such as a protein, then special preparation techniques may be required to minimize the exposure of the active agent to damaging conditions. Such techniques are disclosed in, for example, U.S. Pat. Nos. 5,620,697 (Tormala et al., assigned to Orion-Yhtyma Oy and Leiras Oy), which discloses ultrasonic melting to form matrix-type pharmaceutical compositions, and 5,518,730 (Fuisz, assigned to Fuisz Technologies, Inc.), which discloses melt-spinning, both of which techniques are designed to minimize the exposure of the polymer and active to elevated temperatures. Other methods are disclosed in the patents and literature references cited elsewhere in this application.

An alternate method for the incorporation and release of sensitive therapeutic agents is to use bioerodible polymers that have physical properties tailored for this incorporation. For example, the polymer may be chosen so that it is semi-solid and has an ointment-like consistency, rather than being fully solid. Thus, a polymer may be chosen that has a very high viscosity at normal body temperature of 37° C. so that little if any deformation takes place at that temperature. However, the viscosity of the polymer may decrease substantially at temperatures no higher than 45° C., or preferably by 40° C., so that injection of the material may be possible at a temperature at which the active agent retains its activity.

The composition obtained from any of the above methods can be readily processed into a variety of shapes and forms for implantation, insertion or placement on the body or into body cavities or passageways. For example, the polymer composition may be injection molded, extruded or compressed into a thin film or made into devices of various geometric shapes or forms such as flat, square, round, cylindrical, tubular, disc, ring and the like. Rod- or pellet-shaped devices may be implanted through a trocar, such as is known for Norplant® implants, and these or other shapes may be implanted by minor surgical procedures. Alternatively, a device may be implanted following a major surgical procedure such as tumor removal in the surgical. treatment of cancer.

The polymer composition may also be injected by syringe subcutaneously or intramuscularly as particles of 0.1 $\mu$ to 1000$\mu$, preferably 0.5 $\mu$ to 200$\mu$, and more preferably 1 $\mu$ to 150 $\mu$ suspended in a pharmaceutically acceptable injection base. Liquid vehicles useful for suspending the drug-polymer composition for injection include isotonic saline solution or oils (such as corn oil, cottonseed oil, peanut oil and sesame oil) which, if desired, may contain other adjuvants.

Another injectable dosage form may be prepared from an active agent mixed in with a polymer of the present invention which has an ointment-like consistency. Such a dosage form may be administered by injection with or without a solvent.

The polymer composition administered by either injection or implantation undergoes bioerosion in the body into non-toxic and non-reactive materials. By controlling the number of hydrolyzable bonds in the polymer, the active agent may be released at a desired rate. Implants prepared from the present polymers in which the polymer constitutes the matrix containing an active agent also have the advantage that they do not require removal because of the bioerodibility of the polymer.

In some cases, particles with cores of the pure active agent coated with various thicknesses of the present polymer may be preferred for sustained delivery of the active agent. Coating or encapsulation of discrete particles of the active agent may be accomplished by conventional methods which are all well-known to the person skilled in the art. For example, finely divided drug particles may be suspended in a solvent system (in which the drug is not soluble) containing the dissolved polymer and other excipients, followed by spray drying. Alternatively, the drug particles may be placed in a rotating pan or a fluid-bed dryer and the polymer dissolved in a carrier solvent is sprayed onto the drug particles until a suitable coating quantity is deposited on the particles to give a desired thickness. The coating may also be achieved by suspending the drug particles in a solvent system containing the dissolved polymer followed by adding to the suspension a non-solvent causing the polymer to precipitate and form a coating over the drug particles.

For the sustained release compositions, because the active agent will be released over a controlled period of time, the agent usually is present in an amount which is greater than the conventional single dose. The relative proportions of the active agent and the polymer can vary over a wide range (e.g., 0.1 to 50 weight percent) depending on the therapeutic agent and the desired effect.

Sustained compositions of cosmetic and agricultural agents may also be prepared by any one of the methods as described above, using the polymers of the present invention.

The solid polymers (those containing a high percentage of the "hard" unit) are also useful for a variety of orthopedic applications. For example, they can be used as fracture fixation devices for repair of osteochondral defects, ligament and tendon reconstructions and bone substitutes. In addition, the fact that the present polymers permit simultaneous selection of both a desired level of their mechano-physical state and a desired rate of bioerodibility, also renders them attractive as grafts or scaffolds on which cells can be cultured in vitro prior to implantation to regenerate tissues. Tissues which can be regenerated using this approach include but not limited to, bone, tendon, cartilage, ligaments, liver, intestine, ureter and skin tissues. For example, the polymers may be used to regenerate skin for patients with burns or skin ulcers. Cartilages may be repaired by first isolating chondrocytes from a patient (or a donor), allowing them to proliferate on the scaffolds prepared from the present polymer and re-implanting the cells in the patient.

The polymer scaffolds or implants may further contain other biologically active substances or synthetic inorganic materials such as reinforcing filler material for enhancing the mechanical properties of the scaffolds or implants (e.g. calcium sodium metaphosphate fibers), antibiotics or bone growth factors to induce and/or promote orthopedic restoration and tissue regeneration.

EXAMPLES

Example 1

Preparation of Diketene Acetal of Formula (II)

Synthesis of 3,9-di(ethylidene)-2,4,8,10-tetraoxaspiro [5.5] undecane (DETOSU)

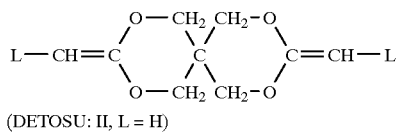

(DETOSU: II, L = H)

A 3-liter, 3-necked flask fitted with a mechanical stirrer, argon inlet tube, thermometer and rubber septum was charged with 1.2 L of ethylenediamine. The flask was cooled with ice water and the contents kept at about 8° C. under an argon atmosphere. A hexane solution of n-butyllithium (130 g, 2 moles) was added through a stainless steel hypodermic U-tube pushed through the rubber septum using carefully controlled argon pressure over one hour. Next, a mixture of 3,9-divinyl-2,4,8,10-tetraoxaspiro[5.5]undecane (available from Aldrich Chemical Company, Inc., Milwaukee, Wis., USA) (530 g, 2.5 moles) and 0.5 L of ethylenediamine was cooled to 8° C. and added to the flask. After stirring at 8° C. for 3 hours, the reaction mixture was poured into 3 L of ice water with vigorous stirring. The aqueous mixture was extracted twice with 1 L portions of hexane. The combined hexane extracts were washed three times with 1 L portions of water, dried over anhydrous magnesium sulfate and filtered under suction. The filtrate was evaporated to dryness on a rotary evaporator to give crude material (413 g, 78%) containing 90% of 3,9-di(ethylidene)-2,4,8,10-tetraoxaspiro [5.5]undecane (DETOSU).

The crude product was dissolved in 2 L of hexane containing 10 mL of triethylamine and the solution placed in a 4 L filter flask, sealed and stored in a freezer at −20° C. for two days. The crystals thus formed were collected by basket centrifugation at −5° C. under an argon atmosphere. Distillation of the brownish product through a 12-inch Vigreaux column at reduced pressure gave 3,9-di(ethylidene)-2,4,8, 10-tetraoxaspiro[5.5]undecane (313 g, 61% yield) as a colorless liquid, boiling point 82° C. (0.1 torr) which crystallized at room temperature, with melting point 30° C. and a characteristic IR band at 1700 cm$^{-1}$.

Example 2

Preparation of Diols of Formula III(a), III(b) or III(c)

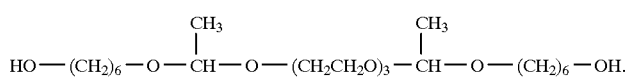

2(a)

Triethyleneglycol divinyl ether (24.631 g, 100 mmoles) and 1,6-hexanediol (23.636 g, 200 mmoles) were dissolved in 100 mL of tetrahydrofuran. To this solution was added a catalytic amount (approximately 10 mg) of p-toluenesulfonic acid, and the mixture was refluxed under anhydrous conditions for 30 minutes. Evaporation of the solvent yielded the product shown above as a colorless oil.

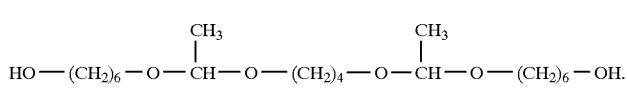

2(b)

1,4-Butanediol divinyl ether (14.22 g, 100 mmoles) and 1,6-hexanediol (23.636 g, 200 mmoles) were reacted according to the procedure of Example 2(a), yielding the product shown above as an oil.

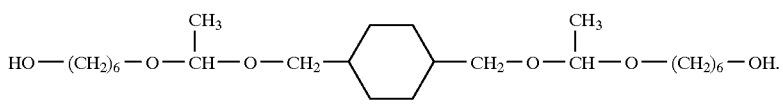

2(c)

1,4-Cyclohexanedimethanol divinyl ether (19.629 g, 100 mmoles) and 1,6-hexanediol (23.636 g, 200 mmoles) were reacted according to the procedure of Example 2(a), yielding the product shown above as an oil.

distillation. Evaporation of the solvent yielded the product shown above as a solid material.

Using analogous procedures, the following additional diols were synthesized:

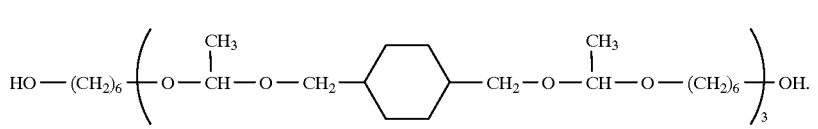

2(d)

1,4-Cyclohexanedimethanol divinyl ether (5.889 g, 30 mmoles) and 1,6-hexanediol (4.727 g, 40 mmoles), were reacted according to the procedure of Example 2(a), yielding the product shown above as a viscous oil.

2(h)

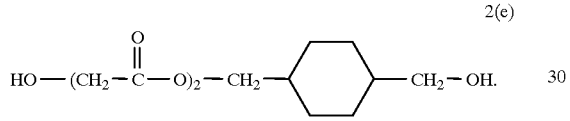

2(e)

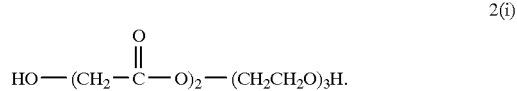

2(i)

Under anhydrous conditions, 1,4-cyclohexanedimethanol (14.42 g, 100 mmoles) and glycolide (11.6 g, 100 mmoles) were weighed into a 100-mL round bottom flask. The flask was stoppered with a rubber septum, then heated in an oil bath at 180° C. for 24 hours. The product shown above was obtained as a viscous oil.

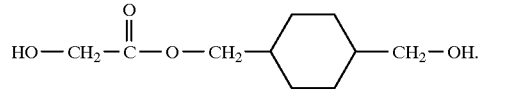

2(j)

Example 3

Preparation of Polymer of Formula I

The following syntheses illustrate the preparation of polymers of this invention from the starting materials whose syntheses are shown above.

3(a). The polymer in this example was prepared from DETOSU, the diol of Example 2(a) above, trans-cyclohexanedimethanol (referred to hereafter as t-CDM), and the diol of Example 2(h) above. The molar ratio of the four components (DETOSU:diol 2(a):t-CDM:diol 2(h)) was 100:9:90:1.

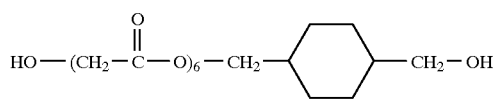

2(f)

1,4-Cyclohexanedimethanol (2.88 g, 20 mmoles) and glycolide (6.96 g, 60 mmoles) were reacted according to the procedure of Example 2(e), yielding the product shown above as a low-melting solid.

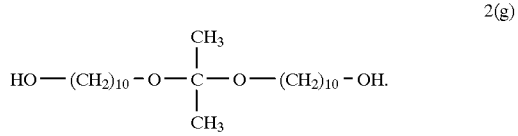

2(g)

Under anhydrous conditions, 1,10-decanediol (17.43 g, 100 mmoles) and 2,2-dimethoxypropane (5.10 g, 50 mmoles) were weighed into a 250 mL flask. To the flask was added cyclohexane (150 mL) and a catalytic amount of p-toluenesulfonic acid (20 mg). The flask was adapted to a distillation column, then heated in an oil bath at 105° C. for 24 hours to remove methanol by-product by azeotropic Under rigorously anhydrous conditions, DETOSU (8.49 g, 40 mmoles), diol 2(a) (1.738 g, 3.6 mmole), t-CDM (5.192 g, 36 mmoles), and diol 2(h) (0.094 g, 0.4 mmole) were weighed into a 250 mL round bottom flask, and the mixture dissolved in anhydrous tetrahydrofuran (75 mL). To this solution was added a p-toluenesulfonic acid solution in tetrahydrofuran (5 drops, 40 mg/mL) to initiate the polymerization. The solution came to a boil within a few minutes. The solution was allowed to cool to room temperature, then slowly poured with vigorous stirring into an excess of methanol (800 mL) containing triethylamine (1 mL) as a stabilizer. The precipitated polymer was collected and dried overnight in a vacuum oven at 40° C. The yield was 11.8 g. The material was solid with a molecular weight of 46,500 and a glass transition temperature of 33° C.

3(b). The polymer in this example was prepared from DETOSU, the diol of Example 2(b) above, t-CDM, and the diol of Example 2(h) above, at a molar ratio of 100:9:90:1.

Following the procedure of Example 3(a), DETOSU (8.49 g, 40 mmoles), diol 2(b) (1.363 g, 3.6 mmoles), t-CDM (5.192 g, 36 mmoles), and diol 2(h) (0.094 g, 0.4 mmole) were allowed to react. The reaction yielded 14.3 g of a solid material having a molecular weight of 74,000 and a glass transition temperature of 30° C.

3(c). The polymer in this example was prepared from DETOSU, the diol of Example 2(a) above, t-CDM, and the diol of Example 2(h) above, at a molar ratio of 100:39:60:1.

Following the procedure of Example 3(a), DETOSU (8.49 g, 40 mmoles), diol 2(a) (7.541 g, 15.6 mmoles), t-CDM (3.46 g, 24 mmoles), and diol 2(h) (0.094 g, 0.4 mmole) were allowed to react. The reaction yielded 18.46 g of a tacky solid material having a molecular weight of 37,000.

3(d). The polymer in this example was prepared from DETOSU, the diol of Example 2(a) above, and the diol of Example 2(h) above, at a molar ratio of 100:99:1.

Following the procedure of Example 3(a), DETOSU (8.49 g, 40 mmoles), diol 2(a) (19.117 g, 39.6 mmoles), and diol 2(h) (0.094 g, 0.4 mmole) were allowed to react. The reaction yielded 18.9 g of an ointment-like material having a molecular weight of 49,000.

3(e). The polymer in this example was prepared from DETOSU, the diol of Example 2(a) above, and the diol of Example 2(h) above, without including t-CDM. The molar ratio of DETOSU:diol 2(a):diol 2(h) was 100:90:10, to give a product containing no residues of t-CDM.

Following the procedure of Example 3(a), DETOSU (8.49 g, 40 mmoles), diol 2(a) (17.38 g, 36 mmoles), and diol 2(h) (0.94 g, 4 mmole) were allowed to react. The reaction yielded a viscous liquid material having a molecular weight of 35,000.

3(f). The polymer in this example was prepared from DETOSU, the diol of Example 2(e) above, and t-CDM, at a molar ratio of 100:10:90.

Following the procedure of Example 3(a), DETOSU (8.49 g, 40 mmoles), diol 2(e) (1.04 g, 4 mmole) and t-CDM (5.19 g, 36 mmoles) were allowed to react. The reaction yielded 14.2 g of a solid material having a molecular weight of 84,000.

3(g). The polymer in this example was prepared from DETOSU, the diol of Example 2(e) above, and t-CDM, at a molar ratio of 100:50:50.

Following the procedure of Example 3(a), DETOSU (8.49 g, 40 mmoles), diol 2(e) (5.21 g, 20 mmoles) and t-CDM (2.884 g, 20 mmoles) were allowed to react. The reaction yielded a solid material having a molecular weight of 69,000.

3(h). The polymer in this example was prepared from DETOSU and the diol of Example 2(e) above, without including t-CDM. The molar ratio of DETOSU to the diol was 100:100.

Following the procedure of Example 3(a), DETOSU (8.49 g, 40 mmoles) and diol 2(e) (10.412 g, 40 mmoles) were allowed to react. The reaction yielded a solid material having a molecular weight of 105,000.

3(i). The polymer in this example was prepared from DETOSU and the diol of Example 2(f) above, without including t-CDM. The molar ratio of DETOSU to the diol was 100:100.

Following the procedure of Example 3(a), DETOSU (2.12 g, 10 mmoles) and diol 2(f) (4.87 g, 10 mmoles) were allowed to react. The reaction yielded a solid material having a molecular weight of 25,000.

3(j). The polymer in this example was prepared from DETOSU, the diol of Example 2(g) above, t-CDM, and the diol of Example 2(h) above, at a molar ratio of 100:9:90:1.

Following the procedure of Example 3(a), DETOSU (8.49 g, 40 mmoles), diol 2(g) (1.391 g, 3.6 mmoles), t-CDM (5.192 g, 36 mmoles), and diol 2(h) (0.094 g, 0.4 mmole) were allowed to react. The reaction yielded a solid material having a molecular weight of 19,000.

Table I summarizes the products of Examples 3(a) through 3(j):

TABLE I

| No. | Molar Ratio of Reactants. | | | | Physical State |
|---|---|---|---|---|---|
| 3 (a) | DETOSU: 100 | 2 (a): 9 | t-CDM: 90 | 2 (h): 1 | Solid ($T_g = 33°$ C.) |
| 3 (b) | DETOSU: 100 | 2 (b): 9 | t-CDM: 90 | 2 (h): 1 g | Solid ($T_g = 30°$ C.) |
| 3 (c) | DETOSU: 100 | 2 (a): 39 | t-CDM: 60 | 2 (h): 1 | Tacky solid |
| 3 (d) | DETOSU: 100 | 2 (a): 99 | — | 2 (h): 1 | Ointment |
| 3 (e) | DETOSU: 100 | 2 (a): 90 | — | 2 (h): 10 | Ointment |
| 3 (f) | DETOSU: 100 | — | t-CDM: 90 | 2 (e): 10 | Solid |
| 3 (g) | DETOSU: 100 | — | t-CDM: 50 | 2 (e): 50 | Solid |
| 3 (h) | DETOSU: 100 | — | — | 2 (e): 100 | Solid |
| 3 (i) | DETOSU: 100 | — | — | 2 (f): 100 | Solid |
| 3 (j) | DETOSU: 100 | 2 (g): 9 | t-CDM: 90 | 2 (h): 1 | Solid |

Further examples of polymers varying in rigidity are illustrated by the use of combinations of three diols (one of which was t-CDM, prepared in a manner analogous to Example 3(a) using DETOSU as the diketene acetal. The diols other than t-CDM are again identified by their example numbers in Example 2, and 1,6-hexanediol (designated "HD") is also included. The relative amounts of the diols in each polymer and the physical states of the polymers are shown in Table II, where two polymers containing only two diols (i.e., lacking t-CDM) are included for comparison.

TABLE II

| No. | Diols: Molar Percentage Relative to DETOSU | | | Physical State |
|---|---|---|---|---|
| 3 (k) | t-CDM: 90 | 2 (a): 9 | 2 (j): 1 | Solid ($T_g = 33°$ C.) |
| 3 (l) | t-CDM: 60 | 2 (a): 39 | 2 (j): | Tacky solid |
| 3 (m) | — | 2 (a): 99 | 2 (j): 1 | Ointment |
| 3 (n) | t-CDM: 90 | 2 (b): 9 | 2 (i): 1 | Solid ($T_g = 30°$ C.) |
| 3 (o) | t-CDM: 60 | 2 (b): 39 | 2 (i): | Tacky solid |
| 3 (p) | — | 2 (b): 99 | 2 (i): 1 | Ointment |
| 3 (q) | t-CDM: 90 | 2 (c): 9 | 2 (h): 1 | Solid ($T_g = 58°$ C.) |
| 3 (r) | t-CDM: 50 | HD: 30 | 2 (e): 20 | Tacky, soft solid |
| 3 (s) | t-CDM: 50 | HD: 30 | 2 (e): 20 | Tacky, soft solid |

Cross-linked polymers may also be prepared as demonstrated in the following examples:

3(t). DETOSU (2.12 g, 10 mmole) and diol 2(i) (1.33 g, 5 mmole) were allowed to react in tetrahydrofuran. After the reaction was completed, tetrahydrofuran was removed to yield a viscous liquid which was then mixed with 1,2,6-hexanetriol (0.456 g, 3.4 mmole). The resulting liquid mixture was heated at 70° C. under anhydrous conditions for 10 hours. The reaction yielded a colorless flexible solid material.

3(u). DETOSU (2.12 g, 10 mmole), 1,6-hexanediol (0.473 g, 4 mmole), diol 2(i) (0.266 g, 1 mmole), and 1,2,6-hexanetriol (0.456 g, 3.4 mmole) were thoroughly mixed. The material was cured following the procedure of Example 3(t) which yielded a flexible solid material.

Example 4

Preparation of Bioerodible Device & Drug Release Study

The following syntheses illustrate further preparations of polymers of this invention, and how the rate of bioerodibility can be controlled by varying the amount of hydrolyzable ester present in the polymer.

(a) A series of polymers were prepared by reacting DETOSU with the α-hydroxy acid containing diol of Example 2(e) and t-CDM, varying the proportion of diol 2(e) to t-CDM while maintaining the total moles of diol equal to the total moles of DETOSU. The molar ratios of diol 2(e) to t-CDM used were 0:100, 10:90, 25:75, 50:50, and 75:25.

The bioerodibility of these polymers was then determined by weight loss tests conducted by pressing each polymer into a film 0.7 mm thick on a Carver press. Discs measuring 7 mm in diameter were then cut from the films. Each disc was placed in 10 mL of pH 7.4 phosphate buffer and incubated at 37° C. Periodically, a disc was removed and dried, and its weight loss was determined gravimetrically.

Figure 2:
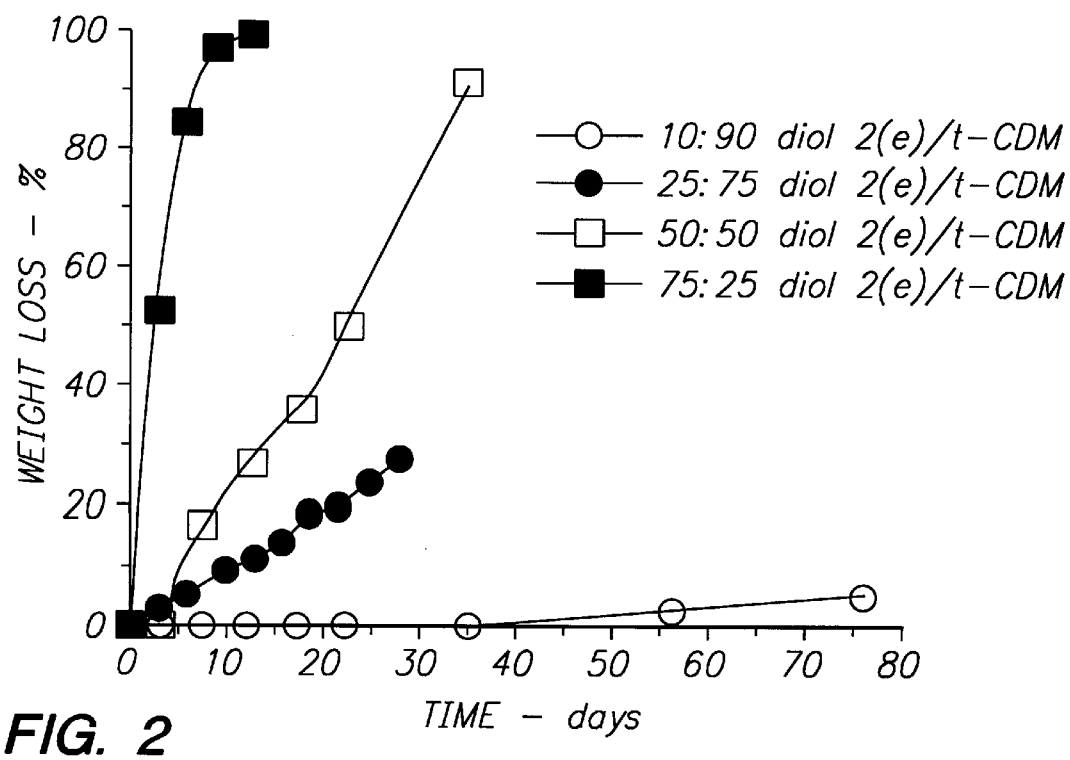
FIG. 2 shows the rate of weight loss of four polymers of this invention containing different proportions of α-hydroxy acid containing units.

The results are plotted in FIGS. 1 and 2. FIG. 1 shows the weight loss over 350 days of a polymer not of this invention containing no α-hydroxy acid containing units (the polymer of DETOSU and t-CDM). FIG. 2 shows the weight loss over 80 days of the four polymers that contain α-hydroxy acid containing units, where the open circles represent the polymer with the 10:90 diol 2(e)/t-CDM molar ratio, the filled circles represent the 25:75 molar ratio, the open squares represent the 50:50 molar ratio, and the filled squares represent the 75:25 molar ratio. The comparison in FIG. 2 and between FIGS. 1 and 2 demonstrates that an increase in the proportion of α-hydroxy acid containing units in the polymer results in an increase in bioerodibility.

(b) A series of polymers were prepared by reacting DETOSU with the α-hydroxy acid containing diol of Example 2(i) and t-CDM, varying the proportion of diol 2(i) to t-CDM while maintaining the total moles of diol equal to the total moles of DETOSU. The molar ratios of diol 2(i) to t-CDM used were 10:90, 20:80, and 25:75.

These polymers were compared in a test measuring the sustained release of 5-fluorouracil. This test was conducted by dissolving each polymer in tetrahydrofuran and adding 5-fluorouracil powder at 10% by weight of the polymer to form a suspension. The suspension was then stirred under a nitrogen flow to remove solvent, and residual solvent was removed by placing the mixture in a vacuum oven. The 5-fluorouracil-impregnated polymer was then pressed into a film and cut into a disc. Each disc was placed in 25 mL of pH 7.4 phosphate buffer at 37° C., and the amount of 5-fluorouracil released was determined by measuring the UV absorption of the buffer solution at 265 nm.

Figure 3:
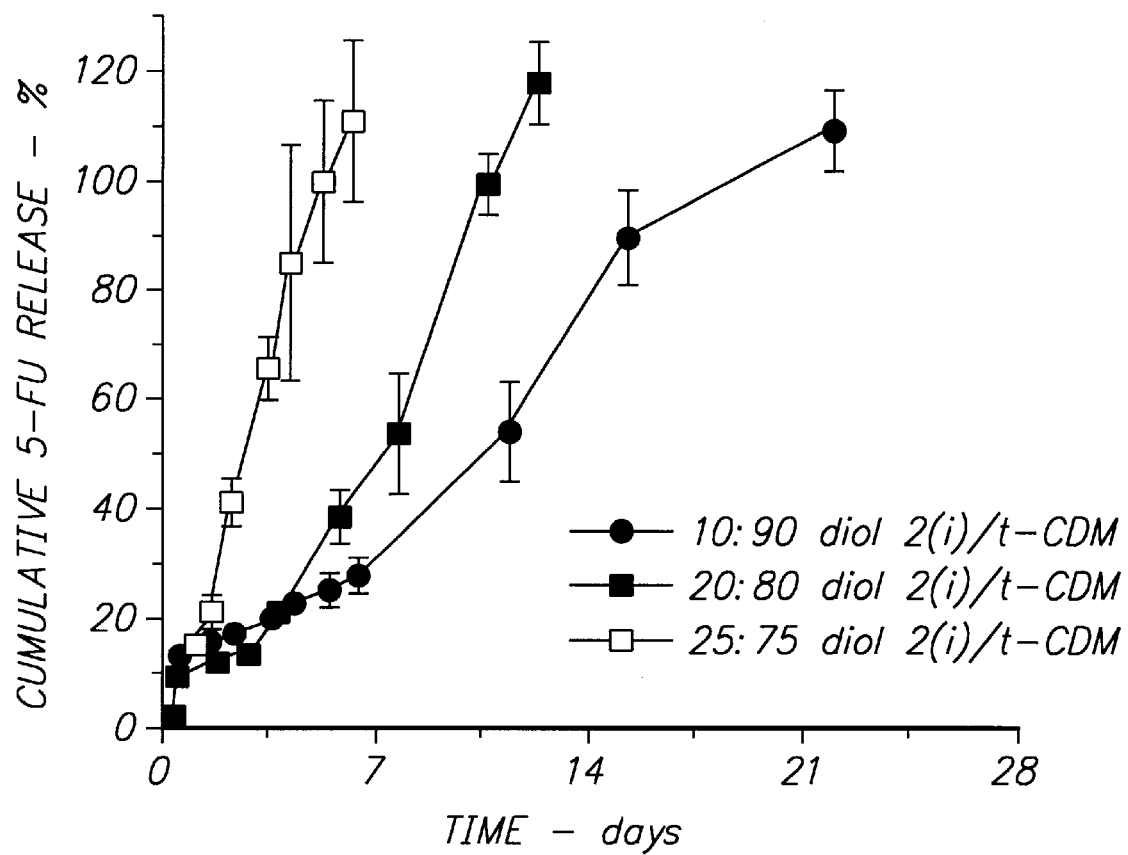
FIG. 3 shows the cumulative release of 5-fluorouracil from three polymers of this invention containing different proportions of α-hydroxy acid containing units.

The results are plotted in FIG. 3, where the filled circles represent the polymer with the 10:90 diol 2(i)/t-CDM ratio, the filled squares represent the 20:80 ratio, and the open squares represent the 25:75 ratio. FIG. 3 demonstrates that an increase in the proportion of α-hydroxy acid containing units in the polymer results in an increase in the rate of release of 5-fluorouracil.

Example 5

Further Preparation of Bioerodible Polymers

Further examples of polymers varying in their rate of bioerodibility are listed in Table III. The polymers were prepared in a manner analogous to Example 3(a), using DETOSU as the diketene acetal. In the first three rows of the table, the diols are triethylene glycol (TEG) and the diol of Example 2(i), and the degree of erodibility decreases as the proportion of diol 2(i) decreases. In the last three rows of the table the diols are t-CDM, 1,6-hexanediol (HD), and the diol of Example 2(h), and the degree of erodibility again decreases as the proportion of diol 2(h) decreases.

TABLE III

| No. | Diols: Molar Percentage Relative to DETOSU | | |
|---|---|---|---|
| 5 (a) | TEG: 0 | 2 (i): 100 | |
| 5 (b) | TEG: 50 | 2 (i): 50 | |
| 5 (c) | TEG: 90 | 2 (i): 10 | |
| 5 (d) | t-CDM: 60 | 2 (h): 40 | HD: 0 |
| 5 (e) | t-CDM: 60 | 2 (h): 20 | HD: 20 |
| 5 (f) | t-CDM: 60 | 2 (h): 5 | HD: 35 |

The foregoing is offered primarily for purposes of illustration. It will be readily apparent to those skilled in the art that the molecular structures, proportions of the reactant materials, methods of use and other parameters of the invention described herein may be further modified or substituted in various ways without departing from the spirit and scope of the invention.

What is claimed is:

1. A polymer of Formula I

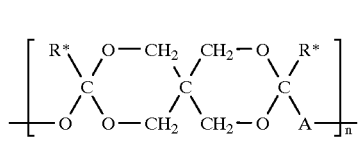

where R* is a $C_1$–$C_4$ alkyl;
each A is selected from the group consisting of —O—$R^1$—, —O—$R^2$—, or (—O—$R^3$)$_q$—, where q is 1 to 20;
n is at least 5; and
$R^1$ is

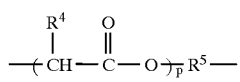

in which
p is 1–10;
$R^4$ is hydrogen or a $C_1$–$C_6$ alkyl; and $R^5$ is

—CH₂—(cyclohexyl)—CH₂—

—(phenyl)—

—(cyclohexyl)—

—(phenyl)—C—(phenyl)—

—(cyclohexyl)—C—(cyclohexyl)—

$-\!\!\!-\!(CH_2CH_2\!-\!O)_{\overline{s}}\,CH_2CH_2\!-\!\!\!-$  or $-\!\!\!-\!(CH_2)_{\overline{t}}\!-\!\!\!-$ where:
s is 1 to 100;
t is 1 to 12;

$R^2$ is

—CH₂—(cyclohexyl)—CH₂—

—(phenyl)—

—(cyclohexyl)—

—(phenyl)—C—(phenyl)—

—(cyclohexyl)—C—(cyclohexyl)—  or when q is 1, $R^3$ is $-\!\!\!-\!(CH_2CH_2\!-\!O)_{\overline{x}}\,CH_2CH_2\!-\!\!\!-$ $-\!\!\!-\!(CH_2)_{\overline{y}}\!-\!\!\!-$  or $$-\!\!\!-\!R^6\!-\!O\!-\!\underset{\underset{R^9}{|}}{\overset{\overset{R^8}{|}}{C}}\!-\!O\!-\!R^7\!-\!\!\!-$$

in which:
x is 1 to 100;
y is 1 to 12;
$R^6$ and $R^7$ are independently a $C_1$–$C_{12}$ alkylene;
$R^8$ is hydrogen or a $C_1$–$C_6$ alkyl; and
$R^9$ is a $C_1$–$C_6$ alkyl; or
$R^8$ and $R^9$ taken together are a $C_3$–$C_{10}$ alkylene; and when q is 2 to 20, each $R^3$ may be the same or different and is —CH₂—(cyclohexyl)—CH₂—

$-\!\!\!-\!(CH_2CH_2\!-\!O)_{\overline{x}}\,CH_2CH_2\!-\!\!\!-$ $-\!\!\!-\!(CH_2)_{\overline{y}}\!-\!\!\!-$ $$-\!\!\!-\!R^6\!-\!O\!-\!\underset{\underset{R^9}{|}}{\overset{\overset{R^8}{|}}{C}}\!-\!O\!-\!R^7\!-\!\!\!-$$  or $$-\!\!\!-\!\underset{\underset{R^{11}}{|}}{\overset{\overset{R^{10}}{|}}{C}}\!-\!\!\!-$$

where x, y, $R^6$, $R^7$, $R^8$ and $R^9$ are as defined above, $R^{10}$ is
hydrogen or a $C_1$–$C_4$ alkyl, and $R^{11}$ is a $C_1$–$C_4$ alkyl;
provided that the polymer comprises at least 0.1 mole percent of units in which A is —O—$R^1$—.

2. The polymer of claim 1 where n is about 5 to about 1000.

3. The polymer of claim 2 where n is about 20 to about 500.

4. The polymer of claim 3 where n is about 30 to about 300.

5. The polymer of claim 1 which comprises about 1 to about 50 mole percent of units in which A is —O—$R^1$—.

6. The polymer of claim 5 which comprises about 2 to about 30 mole percent of units in which A is —O—$R^1$—.

7. The polymer of claim 6 which comprises about 5 to about 30 mole percent of units in which A is —O—$R^1$—.

8. The polymer of claim 7 which comprises about 10 to about 30 mole percent of units in which A is —O—$R^1$—.

9. The polymer of claim 1 where p is 1 to 6.

10. The polymer of claim 9 where p is 1 to 4.

11. The polymer of claim 10 where p is 1 to 2.

12. The polymer of claim 1 where $R^4$ is hydrogen or methyl.

13. The polymer of claim 12 where $R^5$ is

—CH₂—(cyclohexyl)—CH₂—

$-\!\!\!-\!(CH_2CH_2\!-\!O)_{\overline{s}}\,CH_2CH_2\!-\!\!\!-$ where s is 2 to 6; or $-\!\!\!-\!(CH_2)_{\overline{t}}\!-\!\!\!-$ where t is 4 to 6.

14. The polymer of claim 11 where $R^1$ is $$-\!\!\!-\!(CH_2\!-\!\overset{\overset{O}{\|}}{C}\!-\!O)_2\!-\!CH_2\!-\!(cyclohexyl)\!-\!CH_2\!-\!\!\!-$$

-continued

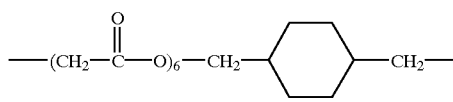

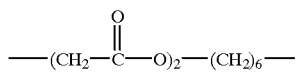

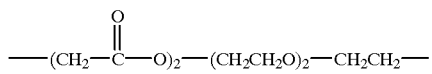

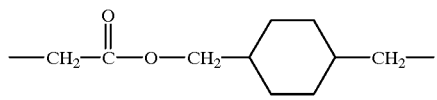

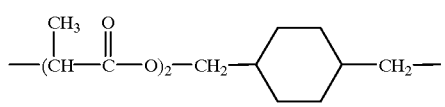

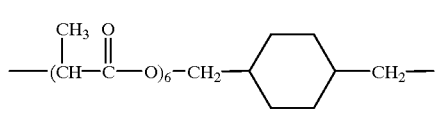

15. The polymer of claim 1 which comprises up to about 20 mole percent of units in which A is —O—$R^2$—.

16. The polymer of claim 1 which comprises about 60 to about 99.9 mole percent of units in which A is —O—$R^2$—.

17. The polymer of claim 1 where $R^2$ is

18. The polymer of claim 1 where q is 1 to 6.

19. The polymer of claim 18 where q is 1 to 3.

20. The polymer of claim 18 where q is 2 to 6 and each $R^3$ is selected from a group consisting of

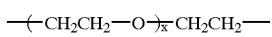

where x is 2 to 6,

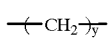

where y is 4 to 6,

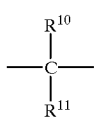

where $R^{10}$ is hydrogen and $R^{11}$ is methyl and

21. The polymer of claim 20 where $(-O-R^3)_q-$ is

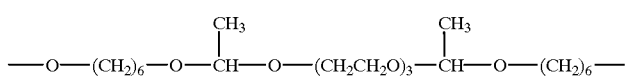

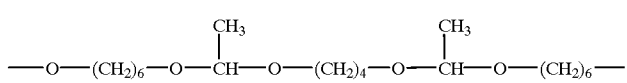

or

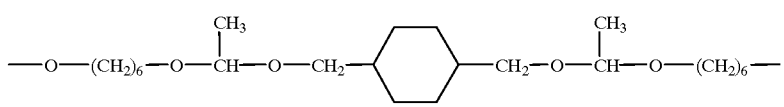

22. The polymer of claim 19 where q is 1 and $R^3$ is

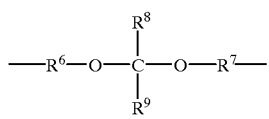

in which both $R^6$ and $R^7$ are an unbranched $C_4$–$C_{12}$ alkylene, and $R^8$ and $R^9$ are both methyl.

23. The polymer of claim 22 where $R^6$ and $R^7$ are both an unbranched $C_{10}$ alkylene.

24. A process for preparing a polymer of Formula I

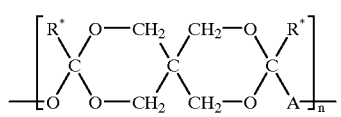 (I)

where $R^*$ is a $C_1$–$C_4$ alkyl;
each A is selected from the group consisting of —O—$R^1$—, —O—$R^2$—, or (—O—$R^3$)$_q$—, where q is 1 to 20;
n is at least 5; and
$R^1$ is

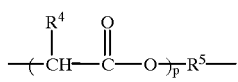

in which:
p is 1–10;
$R^4$ is hydrogen or a $C_1$–$C_6$ alkyl; and
$R^5$ is

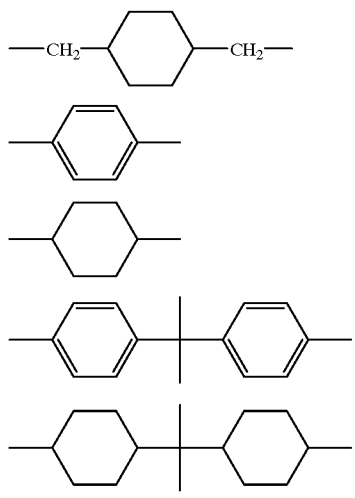

where:
s is 1 to 100;
t is 1 to 12;

$R^2$ is

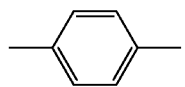

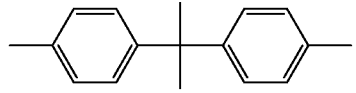

or

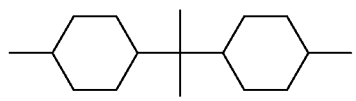

when q is 1, $R^3$ is

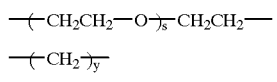

or

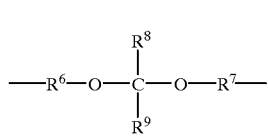

in which:
x is 1 to 100;
y is 1 to 12;
$R^6$ and $R^7$ are independently a $C_1$–$C_{12}$ alkylene;
$R^8$ is hydrogen or a $C_1$–$C_6$ alkyl; and
$R^9$ is a $C_1$–$C_6$ alkyl; or
$R^8$ and $R^9$ taken together are a $C_3$–$C_{10}$ alkylene; and
when q is 2 to 20, each $R^3$ may be the same or different and is

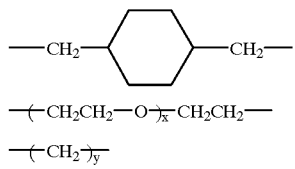

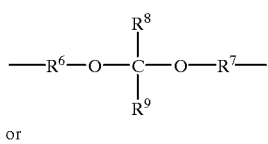

or

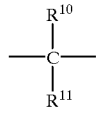

where x, y, $R^6$, $R^7$, $R^8$ and $R^9$ are as defined above, $R^{10}$ is hydrogen or a $C_1$–$C_4$ alkyl, and $R^{11}$ is a $C_1$–$C_4$ alkyl;
provided that the polymer comprises at least 0.1 mole percent of units in which A is —O—$R^1$—;

the process comprising reacting a diketene acetal of Formula II

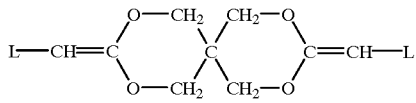

in which L is hydrogen or a $C_{1-3}$ alkyl;
with a diol of Formula III(a) or a mixture of two or more diols of Formulas III(a), III(b) or III(c):

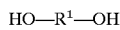   III(a)

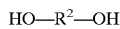   III(b)

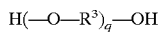   III(c)

provided that at least 0.1 mole percent of the total diol mixture is a diol of Formula III(a).

25. A polymer that is the product of a reaction between:
(a) a diketene acetal of Formula II

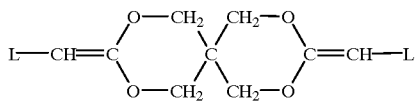

in which L is hydrogen or a $C_{1-3}$ alkyl; and
(b) a polyol or mixture of polyols in which at least 0.1 mole percent of the total polyol content is a diol of the formula HO—$R^1$—OH where $R^1$ is

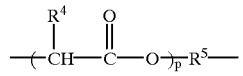

in which:
p is 1–10;
$R^4$ is hydrogen or a $C_1$–$C_6$ alkyl; and $R^5$ is

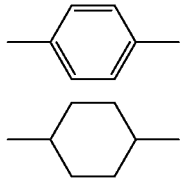

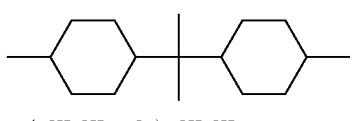

or

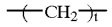

where:
s is 1 to 100; and
t is 1 to 12.

26. The polymer of claim 25 where at least one of the polyols is a polyol having more than two hydroxy functional groups.

27. A composition for the sustained release of an active agent comprising the active agent dispersed in a matrix composed of a polymer of claim 1.

28. The composition of claim 27 where the active agent is a pharmaceutical agent selected from an antigen, a vaccine, a. polypeptide, a hormonal agent, an antipsychotic agent and an anti-neoplastic agent.

29. A device for orthopedic restoration or tissue regeneration comprising a polymer of claim 1.

30. A bioerodible implant comprising a polymer of claim 1.

* * * * *

UNITED STATES PATENT AND TRADEMARK OFFICE
CERTIFICATE OF CORRECTION

PATENT NO. : 5,968,543
DATED : Oct. 19, 1999
INVENTOR(S) : Heller et al.

It is certified that error appears in the above-identified patent and that said Letters Patent is hereby corrected as shown below:

Claim 24, at column 26, line 27 "—(—CH$_2$CH$_2$—O—)$_s$—CH$_2$CH$_2$—" should read -- —(—CH$_2$CH$_2$—O—)$_x$—CH$_2$CH$_2$— --.

Signed and Sealed this

Twenty-fifth Day of July, 2000

Attest:

Attesting Officer

Q. TODD DICKINSON

Director of Patents and Trademarks